(12) United States Patent
Banerjee et al.

(10) Patent No.: US 7,153,905 B2
(45) Date of Patent: Dec. 26, 2006

(54) HYPERBRANCHED DENDRON AND METHODS OF SYNTHESIS AND USE THEREOF

(75) Inventors: Pallab Banerjee, Boston, MA (US); Wilfried Reichardt, Breigan (DE); Ralph Weissleder, Peabody, MA (US); Alexei Bogdanov, Arlington, MA (US)

(73) Assignee: The General Hospital Corporation, Boston, MA (US)

( * ) Notice: Subject to any disclaimer, the term of this patent is extended or adjusted under 35 U.S.C. 154(b) by 69 days.

(21) Appl. No.: 10/806,025

(22) Filed: Mar. 22, 2004

(65) Prior Publication Data

US 2005/0079149 A1    Apr. 14, 2005

Related U.S. Application Data

(60) Provisional application No. 60/456,533, filed on Mar. 21, 2003.

(51) Int. Cl.
C08F 8/30 (2006.01)
(52) U.S. Cl. ............ 525/92 B; 525/178; 525/179; 525/330.5; 525/54; 428/78.08; 428/498
(58) Field of Classification Search ........... 525/92 B, 525/178, 179, 330.5, 54; 424/78.08, 497, 424/498
See application file for complete search history.

(56) References Cited

U.S. PATENT DOCUMENTS

| | | | |
|---|---|---|---|
| 4,587,329 | A | 5/1986 | Tomalia et al. |
| 5,338,532 | A | 8/1994 | Tomalia et al. |
| 5,460,831 | A | 10/1995 | Kossovsky et al. |
| 5,514,764 | A | 5/1996 | Frechet et al. |
| 5,527,524 | A | 6/1996 | Tomalia et al. |
| 5,661,025 | A | 8/1997 | Szoka et al. |
| 5,714,166 | A | 2/1998 | Tomalia et al. |
| 5,739,218 | A | 4/1998 | Dvornic et al. |
| 5,788,989 | A | 8/1998 | Jansen et al. |
| 5,902,863 | A | 5/1999 | Dvornic et al. |
| 5,919,442 | A | 7/1999 | Yin et al. |
| 5,962,427 | A | 10/1999 | Goldstein et al. |
| 6,013,240 | A | 1/2000 | Behr et al. |
| 6,288,197 | B1 | 9/2001 | Youngs et al. |
| 6,319,715 | B1 | 11/2001 | Luo et al. |
| 6,322,802 | B1 | 11/2001 | Prusiner et al. |
| 6,331,296 | B1 | 12/2001 | Prusiner et al. |
| 6,419,916 | B1 | 7/2002 | Prusiner et al. |
| 6,475,994 | B1 | 11/2002 | Tomalia et al. |
| 6,517,855 | B1 | 2/2003 | Prusiner et al. |
| 2001/0011109 | A1 | 8/2001 | Tomalia et al. |
| 2002/0123609 | A1 | 9/2002 | Frechet et al. |
| 2002/0146830 | A1 | 10/2002 | Esuvaranathan et al. |
| 2003/0004312 | A1 | 1/2003 | Prusiner et al. |

FOREIGN PATENT DOCUMENTS

| | | |
|---|---|---|
| EP | 0780152 | 6/1997 |
| WO | WO 99/34908 | 7/1999 |
| WO | WO 01/76633 | 10/2001 |

OTHER PUBLICATIONS

Pelta, J. et al., "DNA Aggregation Induced by Polyamines and Cobalthexamine," J Biol Chem., 271, 5656-5662, 1996.
Haensler, J. et al., "Polyamidoamine Cascade Polymers Mediate Efficient Transfection of Cells in Culture," Bioconjugate Chem. 4, 372-379, 1993.
Ohsaki, M. et al., "In Vitro Gene Transfection Using Dendritic Poly(L-lysine)," Bioconjugate Chem. 13, 510-517, 2002.
Kukowska-Latallo, J.F. et al., "Efficient Transfer of Genetic Material into Mammalian Cells Using Starburst Polyamidoamine Dendrimers," Proc. Natl. Acad. Sci. U.S.A., 93, 4897-4902, 1996.
Choi, J.S., et al., "Synthesis of a Barbell-like Triblock Copolymer, Poly(L-lysine) Dendrimer-block-poly(ethylene gylcol)-block-poly(L-lysine) Dendrimer, and its Self-Assembly With Plasmid DNA," J. Am. Chem. Soc., 122, 474-480, 2000.
Boussif, O., et al., "Optimized Galenics Improve In Vitro Gene Transfer With Cationic Molecules Up to 1000-Fold," Gene Therapy 3, 1074-1080, 1996.
Godbey, et al., "Tracking the Intracellular Path of Poly(ethylenimine)/DNA Complexes For Gene Delivery," Proc. Natl. Acad. Sci. U.S.A., 96, 5177-5181, 1999.
Tang, M.X., et al., "In Vitro Gene Delivery by Degraded Polyamidoamine Dendrimers," Biocojugate Chem. 7, 703-714, 1996.

(Continued)

Primary Examiner—James J. Seidleck
Assistant Examiner—Olga Asinovsky
(74) Attorney, Agent, or Firm—Nutter, McClennen & Fish LLP

(57) ABSTRACT

Hyperbranched dendron (HD) polymers are synthesized using low molecular weight polyethyleneimine (BPEI-L) as a core and used for gene delivery. The obtained polymers display low toxicity and efficient gene delivery at low nitrogen-to-phosphate (N/P) ratios. Using successive attachment of ethyleneimine moieties to a PEI core, the polymer has a lower relative ratio of linear-to-branched structures than in the core PEI. The more extensive branching enables the polymer to condense plasmid DNA into nanostructure complexes with a size of less than or equal to about 100 nm. The complexes are stable and efficient in transfecting cells in the presence of serum. Bioluminescent imaging of in vivo gene expression using a luciferase reporter gene performed in live mice showed gene expression in the liver and in submandibular lymph nodes.

32 Claims, 14 Drawing Sheets

OTHER PUBLICATIONS

Lim, Y. B., et al., "Cationic Hyperbranched Poly(amino ester): A Novel Class of DNA Condensing Molecule with Cationic Surface, Biodegradable Three-Dimensional Structure, and Tertiary Amine Groups in the Interior," *J. Am. Chem. Soc.*, 123, 2460-2461, 2001.

Lim, Y. B., et al., "Biodegradable, Endosome Disruptive, and Cationic Network-type Polymer as a Highly Efficient and Nontoxic Gene Delivery Carrier," *Bioconjugate Chem*. 13, 952-957, 2002.

Fischer et al., "A Novel Non-Viral Vector for DNA Delivery Based on Low Molecular Weight, Branched Polyethylenimine: Effect of Molecular Weight on Transfection Efficiency and Cytotoxicity," *Pharm. Res. 16*, 1273-1279, 1999.

Godbey, W.T., et al., "Poly(ethylenimine) and its Role in Gene Delivery," *J. Control. Release. 60*, 149-160, 1999.

Ferrari, S., et al., "ExGen 500 is an Efficient Vector for Gene Delivery to Lung Epithelial Cells In Vitro and In Vivo," *Gene Ther.* 4, 1100-1106, 1997.

Goula, D., et al., Size, Diffusibility and Transfection Performance of Linear PEI/DNA Complexes in the Mouse Central Nervous System, *Gene Ther. 5*, 712-717, 1998.

Goula, D., et al. "Polyethylenimine-based Intravenous Delivery of Transgenes to Mouse Lung," *Gene Ther. 5*, 1291-1295, 1998.

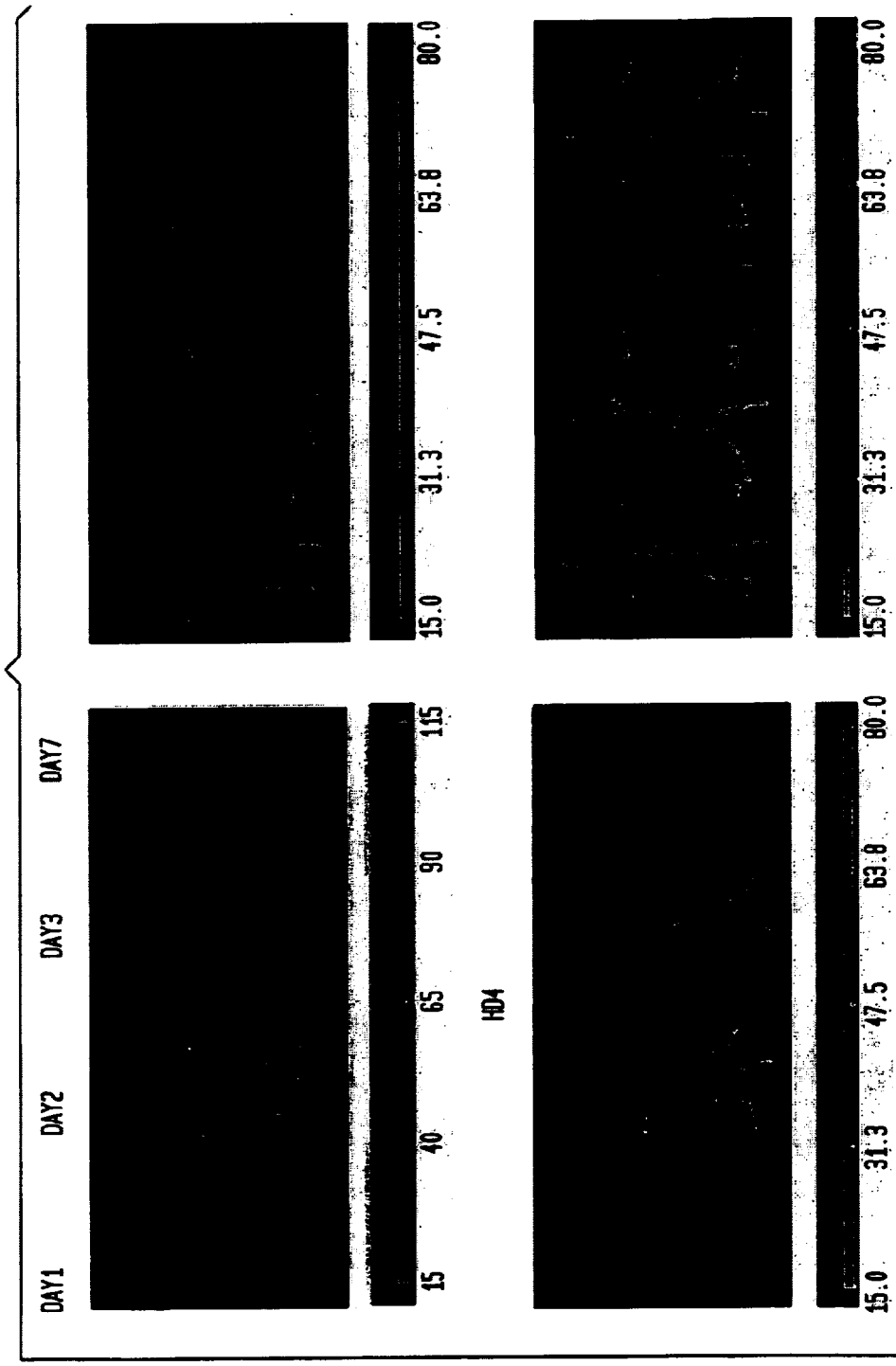

DAY1  DAY3  DAY5  DAY7

HYPERBRANCHED DENDRON AND METHODS OF SYNTHESIS AND USE THEREOF

RELATED APPLICATIONS

This application claims priority from U.S. Provisional Patent Application Ser. No. 60/456,533, filed Mar. 21, 2003 and entitled "Compositions Comprising Hyperbranched Dendron Polymers and Methods of Use Thereof," which is hereby incorporated in its entirety herein.

STATEMENT OF POTENTIAL GOVERNMENT INTEREST

The United States government may have certain rights in this invention by virtue of grant number P50CA086355-03 from the National Cancer Institute.

BACKGROUND OF THE INVENTION

1. Field of the Invention

The invention relates to a new, flexible hyperbranched dendron having multiple binding sites for negatively charged nucleic acids or other polyanions (e.g., DNA), and the synthesis of the hyperbranched dendron. The complexes of hyperbranched polymers and DNA are less than 90 nm in diameter and are very stable for prolonged periods of time; and the polymer material is of low toxicity. The polymer/DNA complexes can bind to and transfect cells in the presence of any added negatively charged medium components (e.g., serum) with unexpectedly high efficiency. The in vitro transfection efficiency using the hyperbranched dendron of the invention is higher than transfection reagents that are currently commercially available. In addition, because of the high transfection efficiency and low cytotoxicity, the hyperbranched dendron shows good in vivo transfection efficiency and includes lasting gene expression.

2. Introduction

Non-viral gene transfer is frequently regarded as a potentially more safe alternative to the viral gene delivery. However, non-viral gene transfer to mammalian cells usually lacks the efficiency typical to that of viral transduction and requires substantial improvement. Non-viral delivery of DNA usually requires condensation with positively charged lipids or polycations to enable binding of polyionic complexes to plasma membrane and further internalization by cells. The condensation ideally yields complexes that could release DNA after the internalization. In recent years several cationic polymers that readily form complexes with DNA (e.g. polylysine, polyethyleneimine or various types of block and graft copolymers) have been investigated as potential nonviral vectors that enable transfer of DNA into mammalian cells. Interactions of a polycation and DNA frequently results in a formation of very compact colloidal complexes which are frequently unstable and may precipitate from solutions [Pelta, J., et al., "DNA aggregation induced by polyamines and cobalthexamine," *J Biol Chem.* 271, 5656–5662 (1996).]. Physical properties of these complexes that define their size and stability depend heavily on chemical structure as well as on physical properties of the polycation.

As research in the area of synthetic carriers for DNA delivery expands beyond the traditional in vitro experiments, various polycations, including branched polyethyleneimine (BPEI), starburst polyamidoamine (PAMAM) dendrimers [Haensler, J., et al., "Polyamidoamine Cascade Polymers Mediate Efficient Transfection of Cells in Culture," *Bioconjugate Chem.* 4, 372–379 (1993); Ohsaki, M., et al., "In vitro gene Transfection using dendritic poly(L-lysine)," *Bioconjugate Chem.* 13, 510–517 (2002); KukowskaLatallo, J. F., et al., "Efficient transfer of genetic material into mammalian cells using Starburst polyamidoamine dendrimers," *Proc. Natl. Acad. Sci. U.S.A.* 93, 4897–4902 (1996); Choi, J. S., et al., "Synthesis of a barbell-like triblock copolymer, poly(L-lysine) dendrimer-block-poly(ethylene glycol)-block-poly(L-lysine) dendrimer, and its self-assembly with plasmid DNA," *J. Am. Chem. Soc.* 122, 474–480 (2000).], as well as hyperbranched polymers are now being closely investigated.

Some of the above polycations have shown high levels of gene transfer in mammalian cell culture. High transfection efficiency of BPEI and PAMAM compared to other polycations is explained by the effect of a "proton sponge" [Boussif, O., et al., "Optimized galenics improve in vitro gene transfer with cationic molecules up to 1000-fold," *Gene Ther.* 3, 1074–1080 (1996)]. This effect is supposedly caused by the protonation of tertiary amines present in the core of those polymers in acidic milieu of endosomes. Godbey et al. ["Tracking the intracellular path of poly(ethylenimine)/DNA complexes for gene delivery," *Proc. Natl. Acad. Sci. U.S.A.* 96, 5177–5181 (1999)] reported that the protonated form of branched PEI or PAMAM may perturb endosomes probably due to membrane activity of cationic polymers or by osmotic effects causing occasional lysis. Haensler et al. (supra) has reported that dendrimers show high level of transfection in a wide variety of cells in culture with low concomitant cytotoxicity. However, in a later study they reported that stringently synthesized and purified, monodisperse PAMAM dendrimers showed low levels of transfection.

Furthermore, the transfection activity of PAMAM dramatically improved after the random degradation by heat treatment in a solvolytic solvent [Tang, M. X., et al., "In vitro gene delivery by degraded polyamidoamine dendrimers," *Bioconjugate Chem.* 7, 703–714 (1996)] leading to a hypothesis that polydisperse "fractured" dendrimers are more flexible than monodisperse PAMAM enabling "fractured" dendrimer to form compact complex with DNA. Interestingly, fractured dendrimers are able to swell when released from DNA. Recently, Lim et al. [Lim, Y. B., et al., "Cationic hyperbranched poly(amino ester): A novel class of DNA condensing molecule with cationic surface, biodegradable three-dimensional structure, and tertiary amine groups in the interior." *J. Am. Chem. Soc.* 123, 2460–2461 (2001); Lim, Y. B., et al., "Biodegradable, endosome disruptive, and cationic network-type polymer as a highly efficient and nontoxic gene delivery carrier," *Bioconjugate Chem.* 13, 952–957 (2002)] reported biodegradable hyperbranched poly(amino esters) with high transfection efficiency and low cytotoxicity in vitro. This polymer is attractive, because unlike PAMAM dendrimer, it degrades within several days at physiological pH and, in addition, can be synthesized more easily than the fractured dendrimer.

The majority of PEI-mediated transfections use a low-branched polymer having MW from 25 kD to 800 kD that show good transfection efficiency in vitro [Boussif, O., et al., "Optimized galenics improve in vitro gene transfer with cationic molecules up to 1000-fold," *Gene Ther.* 3, 1074–1080 (1996); Fischer, D., et al., "A novel non-viral vector for DNA delivery based on low molecular weight, branched polyethylenimine: Effect of molecular weight on transfection efficiency and cytotoxicity," *Pharm. Res.* 16, 1273–1279 (1999); Godbey, W. T., et al., "Poly(ethylenimine) and its role in gene delivery" *J. Control. Release.* 60, 149–160 (1999)]. Unfortunately, high molecular weight PEI has high cytotoxicity that limits its scope of potential applications in vivo. To decrease the cytotoxicity and to increase water solubility of the DNA polymer complex, polyethylene glycol-graft-PEI has been obtained. Grafted PEI has lower transfection efficiency than the non-grafted PEI but the latter drawback is compensated with a low cytotoxicity at high N/P ratio. There appears to be only one published report by Fischer, et al., (supra) describing the synthesis of a low molecular weight non-toxic branched PEI that showed at least two orders of magnitude higher transfection efficiency than a commercially available high molecular weight PEI. However, it is known that despite having a very low cytotoxicity, linear PEI (LPEI) is a less efficient transfection reagent than branched 25K PEI. As tertiary and secondary amine groups appear to cause less toxic effects than primary amine, LPEI is less toxic than branched low molecular weight PEI due to prevalence of secondary amino group. Overall, it appears that LPEI could be a good candidate for in-vitro and in-vivo gene delivery [Ferrari, S., et al., "ExGen 500 is an efficient vector for gene delivery to lung epithelial cells in vitro and in vivo," *Gene Ther.* 4, 1100–1106 (1997); Goula, D., et al., "Size, diffusibility and transfection performance of linear PEI/DNA complexes in the mouse central nervous system," *Gene Ther.* 5,712–717 (1998); Goula, D., et al., "Polyethylenimine-based intravenous delivery of transgenes to mouse lung," *Gene Ther.* 5, 1291–1295 (1998)].

However, none of the previously described non-toxic polycations appear to form sufficiently stable submicron complexes with DNA that could be useful for gene transfer in the presence of serum. The ability to preserve transfection ability in serum is critical for in vivo gene delivery. Therefore, the goals of the present invention include designing a high transfection efficiency polymer system that: 1) would form nanosized, stable complexes with plasmid DNA that would be amenable to a long-term storage; 2) would be efficient at low N/P ratios in presence of serum; 3) would have low cytotoxicity and/or 4) would be useful for in vivo gene delivery.

SUMMARY OF THE INVENTION

The invention provides new transfection agents for both in vitro and in vivo gene delivery in mammalian cells and intact animals, preferably humans.

The invention includes compositions of hyperbranched dendron polymers, characterization thereof, methods of sythesis, and methods of transfection using the hperbranched dendrons.

In one aspect, the invention involves the synthesis of flexible hyperbranched dendron polymers based on a polyethyleneimine core. Synthesis is performed such that several primary amine groups will be at the surface of the dendron, while secondary and tertiary amine groups will be positioned in the core. This positioning of amine groups enables low cytotoxicity and high condensing of negatively charged polymers.

In another aspect, a hyperbranched dendron polymer having a randomly branched structure, a molecular weight of about 10 to 25 kD, and a ratio of secondary to tertiary amine groups of less than or equal to about 1.5 to 1 is provided.

In yet another aspect, the invention includes a hyperbranched dendron polymer made by a process comprising iterative attachment of ethyleneimine moieties to a branched polyethyleneimine core, wherein the process increases the amount of secondary and tertiary amines in the polymer while maintaining a plurality of primary amines on a surface of the polymer.

In another aspect, a complex between a hyperbranched dendron and a nucleic acid is prepared in solution by simple mixing of the two components. As the polymer materials can condense nucleic acids effectively with the formation of nanoparticles, even in the presence of serum, various types of nucleic acids can be effectively delivered to cells by the hyperbranched polymer of the invention.

The complex can be delivered with a reporter gene, such as that encoding firefly luciferase. The reporter can then be detected by whole body luminescence imaging technique. Observation of the expression of the reporter gene has shown the surprising effect of persistent (8 days) of lymph node expression of the marker gene has been observed in mice intravenously injected with ultrasmall complexes of DNA-hyperbranched dendron (diameter of <100 nm).

The complex can be used in vitro in the presence of serum for optimal cell survival. In addition, a low concentration of the hyperbranched dendron is needed for efficient transfection.

The polymer/DNA complex can be administered to animals or humans for in vivo gene expression. Unlike other transfection agents, hyperbranched dendrons do not impart cytotoxicity, thus enabling the prolonged expression of desired genes, both in vitro and in vivo.

In another aspect, the invention includes a method for manufacturing a medicament for use in delivery of a nucleic acid in vivo.

The invention will be understood to include the various embodiments, combinations and sub-combinations described herein, and particularly as recited in the claims appended hereto. In particular, it should be understood that the dependent claims describing specific embodiments of the various aspects of the invention can be applied to each aspect of the invention as appropriate. For example, specific embodiments of the complexes of methods of the invention can also apply to like elements of the method for manufacturing a medicament for use in delivery of a nucleic acid in vivo.

BRIEF DESCRIPTION OF THE FIGURES

The invention will be more fully understood from the following detailed description taken in conjunction with the accompanying drawings in which.

Figure 5A:
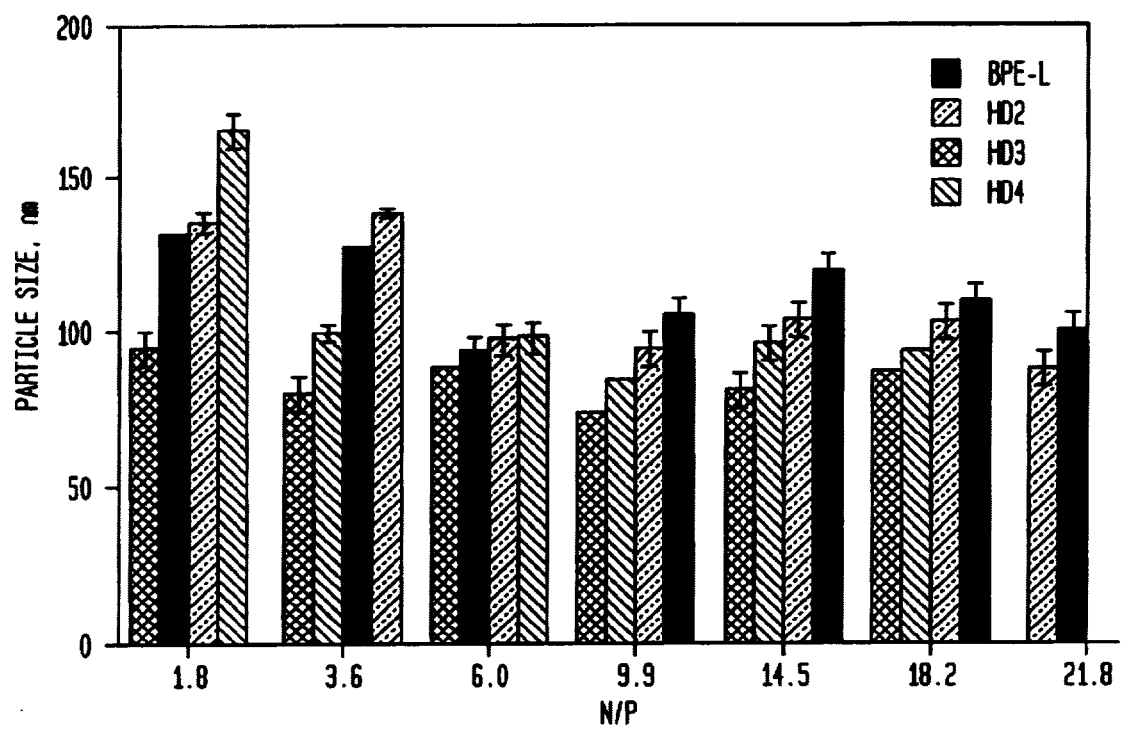
Figure 5B:
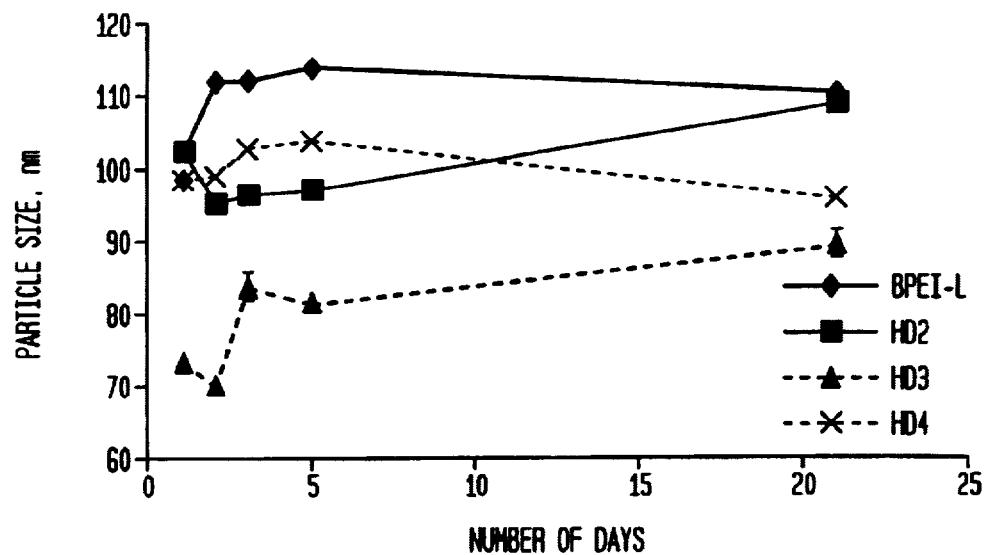
Figure 6:
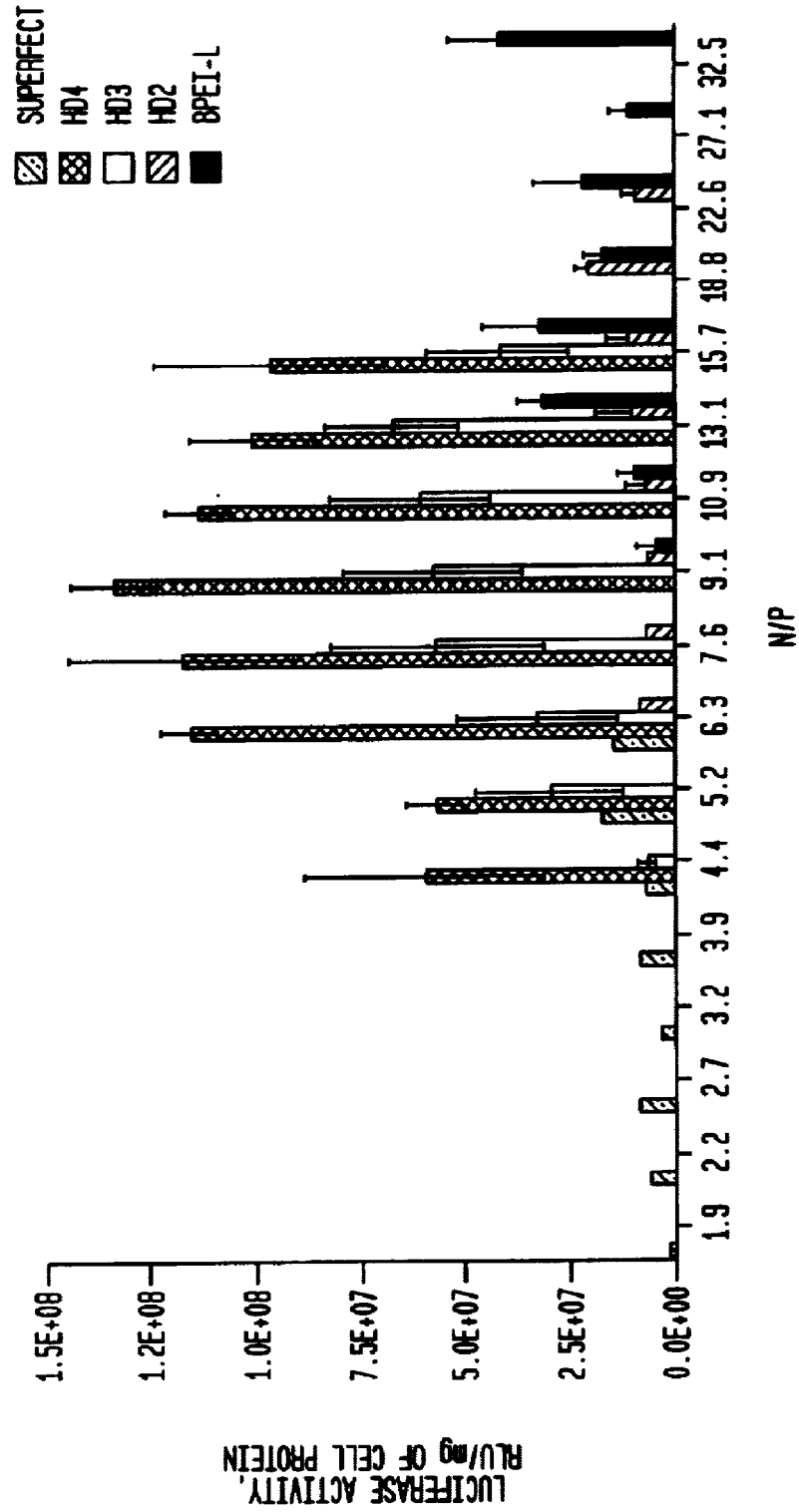
Figure 7:
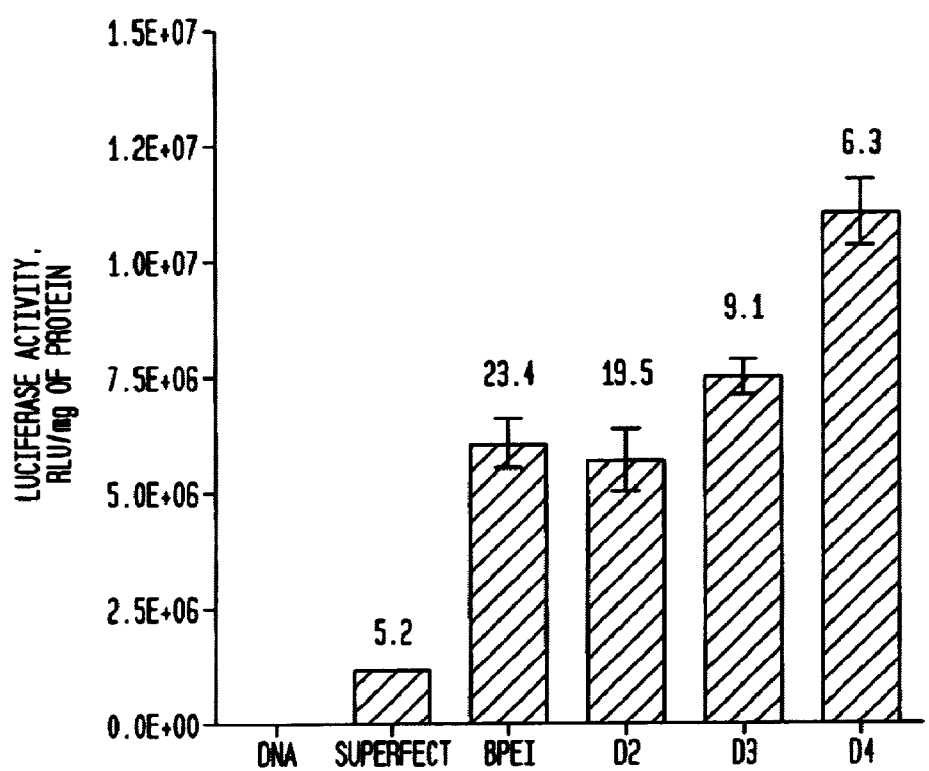
Figure 8A:
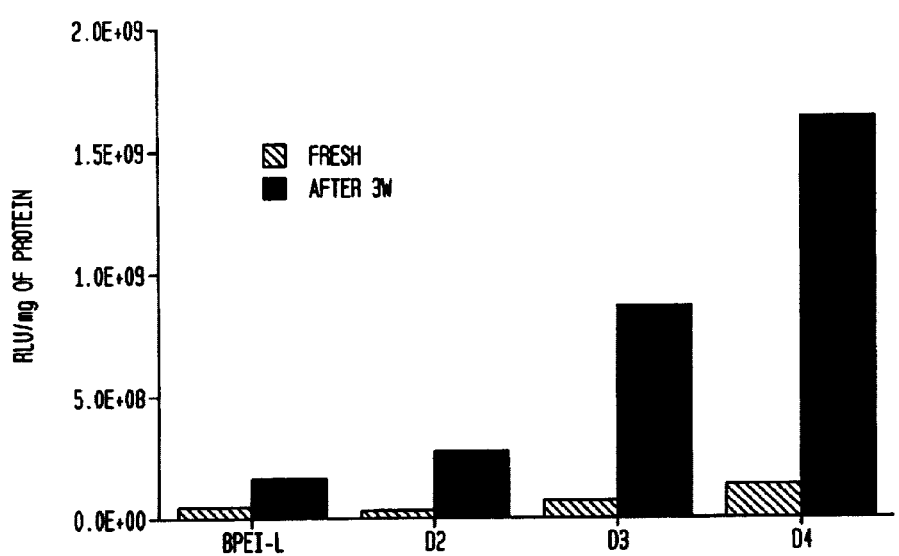
Figure 8B:
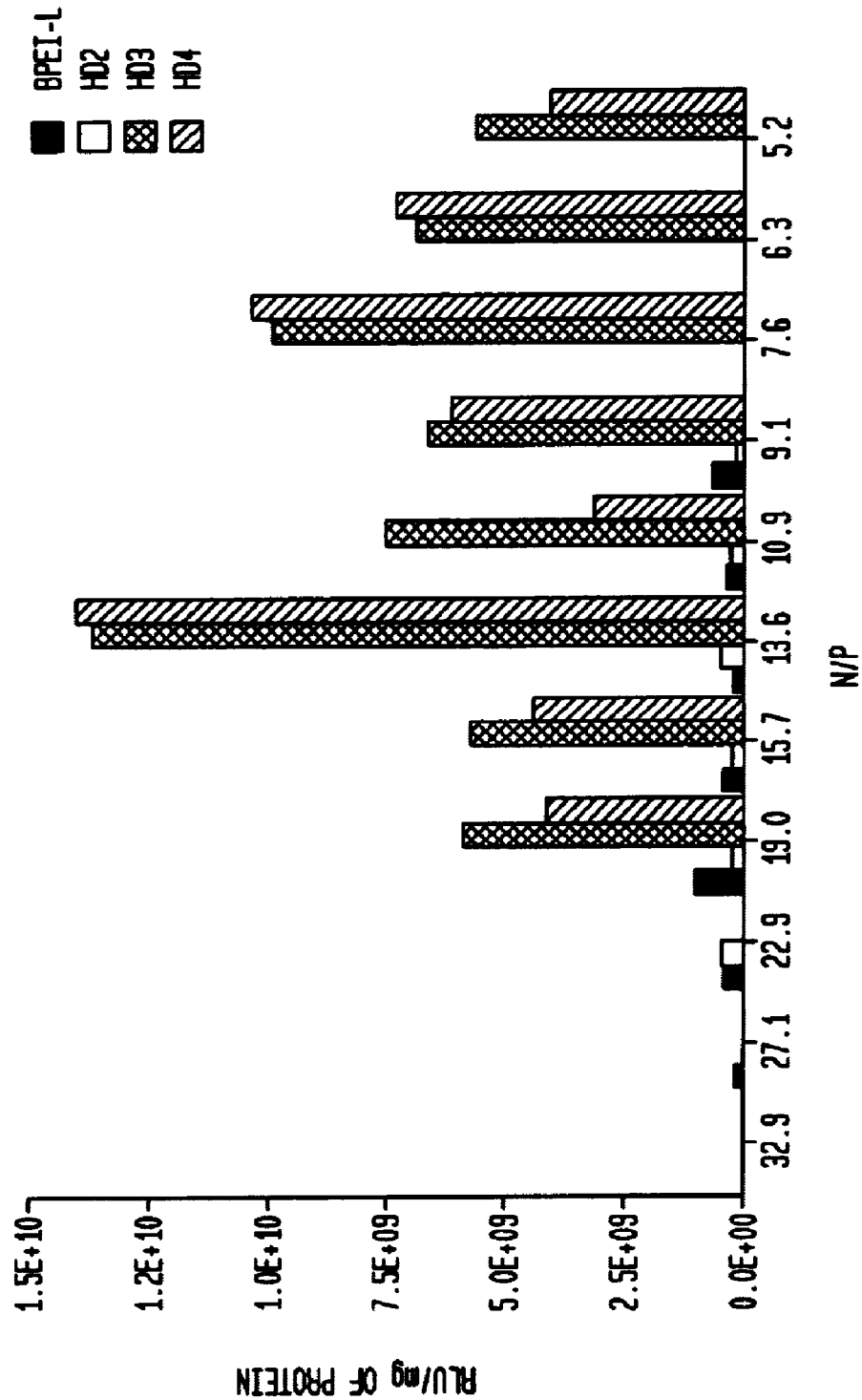
Figure 9B:
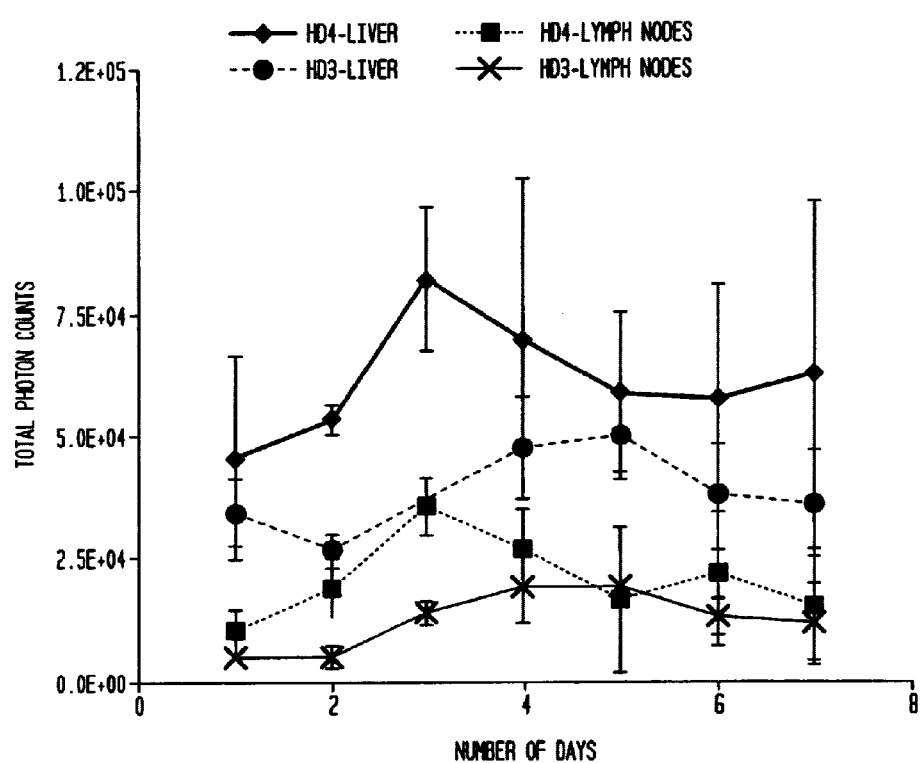
Figure 9C:
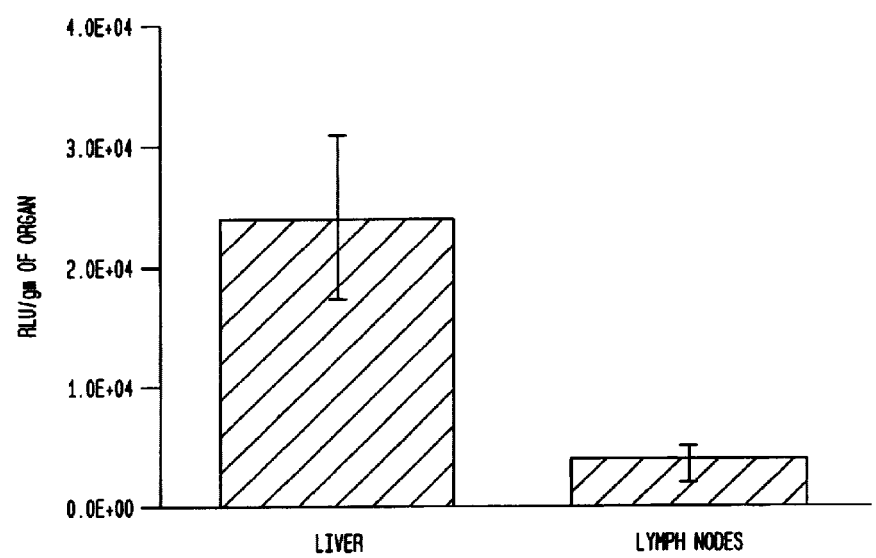
Figure 9D:
Figure 9D:
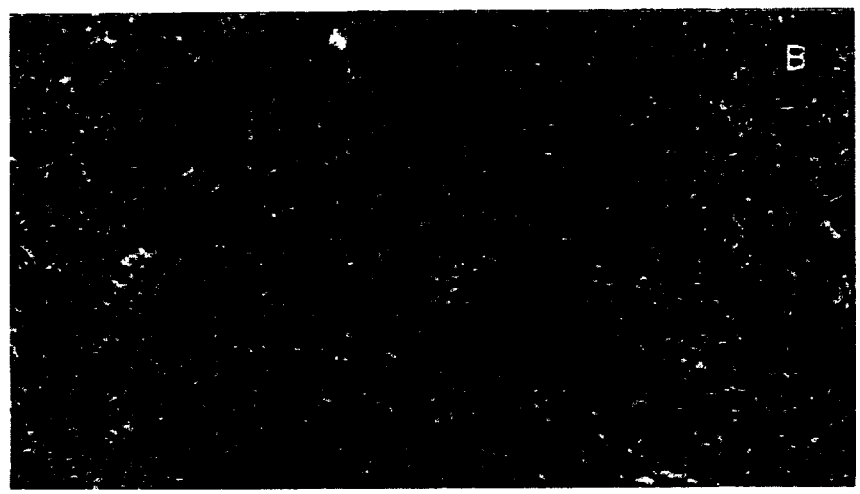
Figure 10:
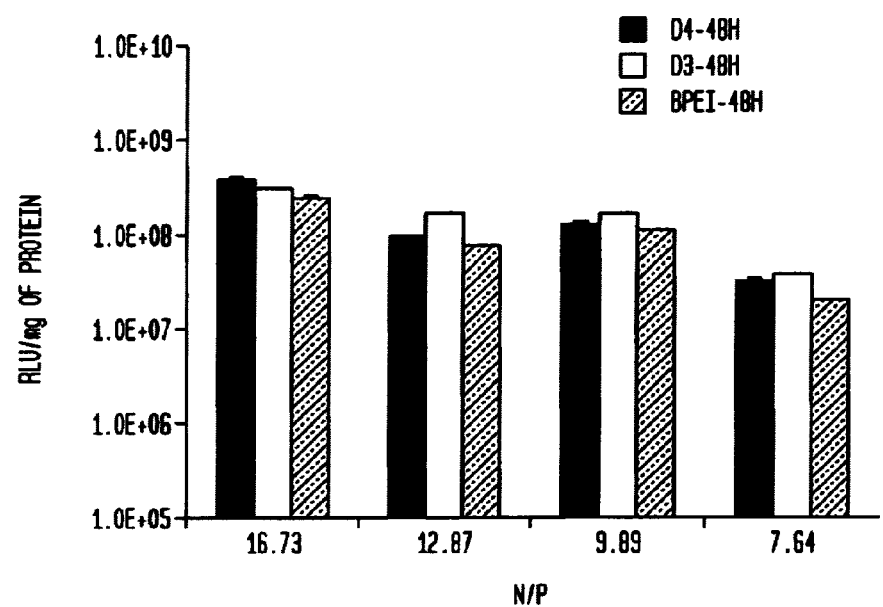
Figure 11:
Figure 11:
Figure 11:
Figure 11:

HD2 (N/P 2.9, 2.6, 2.2, 1.9, 1.5); HD3 (N/P 2.6, 2.2, 1.9, 1.5, 1.1); and HD4 (N/P 1.8, 1.4, 1.05, 0.7);

FIGS. 5A–5B: FIG. 5A shows particle size of complexes prepared using HD4, HD3, HD2 and BPEI-L. FIG. 5B shows variation of particle size with time. The legend denotes BPEI-L at N/P 21.83; HD4 at N/P 6.03; HD3 at N/P 9.9 and HD2 at N/P 18.18. Average sizes obtained in four experiments are shown;

FIG. 6 illustrates a comparison of luciferase expression in vitro using hyperbranched polymers of the invention and Superfect for transfection of COS 1 cells in serum-containing medium at 4 h. Transfection was carried out by adding complexes to the cells containing growth media. Hyperbranched polymer and control Superfect at different N/P ratios. The y-axis represents the relative light measured in (RLU) normalized by the cell protein content. All results shown are the averages of three separate experiments;

FIG. 7 shows in vitro luciferase activity in COS-1 cells transfected with a hyperbranched dendron of the invention for 48 h in serum-containing medium. The x-axis shows the best N/P ratios (n=3 experiments);

FIGS. 8A–8B: FIG. 8A illustrates in vitro luciferase activity in COS-1 cells transfected using a hyperbranched dendron of the invention as a freshly made preparation and after the storage for three weeks at 4 h. FIG. 8B illustrates in vitro luciferase activity of hyperbranched dendron after a 3-week storage at 40C. The transfection was performed at 48 h using COS-1 cells in serum-containing medium. The x-axis represents the best N/P ratios of three independent experiments;

FIGS. 9A–9D: FIG. 9A shows bioluminescence imaging of luciferase expression in living mice using a CCD camera; the image shows the best representative of the group (n=3); fifty μg pCMV-Luc was used for IV injections in all cases; all images were taken for 15 min and shown using two pseudocolor scales: one for HD4 and other for rest of the groups. FIG. 9B illustrates the change of the total photon counts integrated for 15 minutes imaging over 7 days for the case of the HD4 and HD3 groups; the photon counts are averaged for 3 animals. FIG. 9C illustrates ex vivo luciferase activity of lymph nodes and livers of animals injected with HD4-based complex; the results represent averages measured in three animals. FIG. 9D shows the immunohistology of lymph nodes after the administration of HD4/DNA complex (A) or naked DNA (B) intravenously. Fifty μg DNA was used to prepare complexes at N/P 6.3; animals were sacrificed 3 days after injection; polyclonal goat anti-luciferase antibody was used to identify luciferase positive cells followed by a hematoxylin/eosin counterstaining; brown dots (fig A) represent luciferase-positive cells. Magnification is 30 fold;

FIG. 10 illustrates the in vitro luciferase activity in COS-1 cells transfected using a lyophilized powdered complex. The complexes were dissolved in water prior to transfection. The transfection was performed at 48 h in serum-containing medium. The x-axis represents the best N/P ratios of three independent experiments; and FIG. 11 shows bioluminescence imaging of luciferase expression in living mice using a CCD camera illustrating in vivo transfection of mice using the lyophilized powdered complex used in FIG. 10.

DETAILED DESCRIPTION OF AN EMBODIMENT OF THE INVENTION

A variety of polycations (e.g. PAMAM dendrimer, fractured dendrimer) as well as cationic liposomes have been used in the past as non-viral vectors for gene delivery into eukaryotic cells. All these vectors are similar in that they carry positively charged amines that form strong ionic bonds and condense negatively charged DNA. The mechanism of polycation-mediated cell transfection is still remains to be explained in full detail, but it is apparent that DNA compaction by positively charged molecules plays a vital role for achieving high transfection efficiencies. Unfortunately, most of the polymer vectors reported so far can be used mainly for in vitro cell transfection because of the inhibitive effects of serum and/or high in vivo toxicity. To reduce toxicity, several groups achieved limited success by using derivatization of polycations with poly (ethylene glycol) resulting in vectors with low cytotoxicity and low transfection efficiency.

Using the present invention, novel hyperbranched dendron (HD) polymers are synthesized using low molecular weight polyethyleneimine (BPEI-L) as a core and used for gene delivery. The obtained polymers have showed low toxicity and are efficient for gene delivery at low nitrogen-to-phosphate (N/P) ratio. Using successive attachment of ethyleneimine moieties to the PEI core, a process of the invention lowered the relative ratio of linear-to-branched structures in the core PEI from 1.58 to 1.24. This more extensive branching enables to condense plasmid DNA into nanostructures with a size of 70–100 nm. The obtained DNA complexes were stable at least for 3 weeks at 4° C. The HD-DNA complex prepared using the higher secondary and tertiary amine containing dendron exerted a very low cytotoxicity in vitro even if co-incubated with cells for 48 hours. Using firefly luciferase as a marker of protein expression, the inventive HD complexes were efficient in transfecting cells in the presence of serum. Under these conditions the transfection activity at the optimized N/P ratio of 6 is approximately six fold higher than commercially available polycationic transfection reagent. Bioluminescent imaging of in vivo gene expression using luciferase reporter gene performed in live mice shows the expression in the liver and in submandibular lymph nodes. The in vivo gene expression data demonstrates that the HD polymers as in vivo transfection agents could be useful for lymph node gene delivery.

Figure 1:
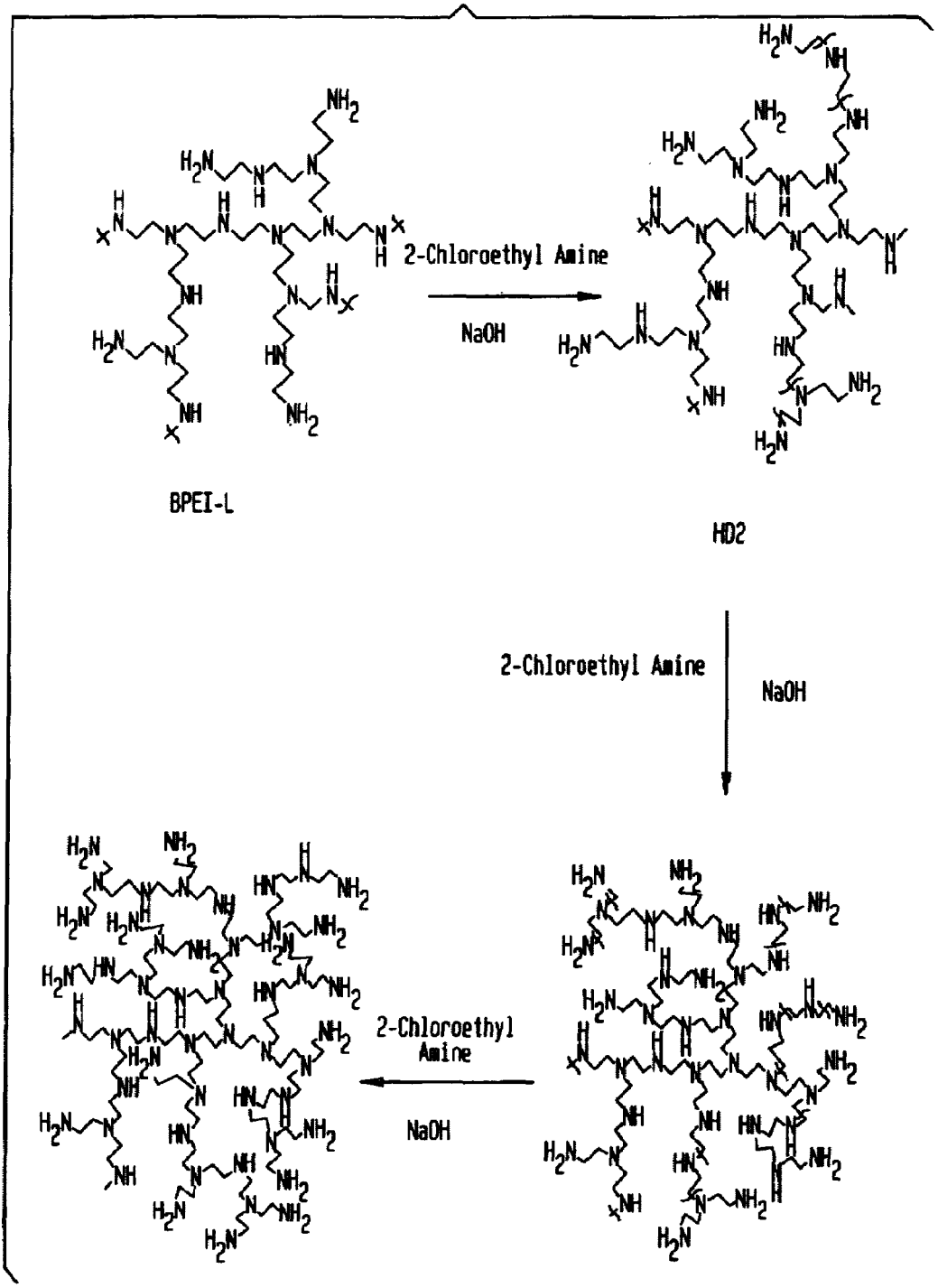
FIG. 1 illustrates a synthesis scheme for a hyperbranched polymer of the invention showing three stages of consecutive aminoethylation of the core BPEI-L to result in HD2, HD3 and HD4, respectively.

While not limiting the invention to any one underlying theory of operation, the invention was developed based upon a hypothesis that the optimization of the balance between the cationic charge density of polymer and DNA phosphates can lead to effective gene transfer and low cytotoxicity. The invention involves the design and development of novel flexible hyperbranched dendrons by controlling branching of the initial branched PEI core polymers. The polymers with pendant hyperbranched functionalities were designed to have similar molecular formulas to those of the idealized dendritic core. However, there was no architectural similarity between dendrimers and the resultant HD polymers (FIG. 1). Hyperbranched polymers usually consist of a mixture of isomers and are polydisperse; they contain varying amounts of linear units with dendritic and terminal building blocks [Magnusson, H., et al., "The effect of degree of branching on the rheological and thermal properties of hyperbranched aliphatic polyethers," *Polymer.* 43, 301–306 (2002)]. Structurally hyperbranched molecules occupy the niche in between the linear and dendrimeric polymers, having more branching than linear macromolecules but less branching than dendrimers. Dendrimers are well-defined, fully branched, monodisperse polymers. Even though hyperbranched polymers are polydisperse and not fully branched, they are more similar to dendrimers than to their linear counterparts. Intrinsic viscosity of a dendrimer and a hyperbranched amidoamine shows that despite structural similarity hyperbranched polymers have much lower intrinsic viscosity than dendrimers [Hobson, L. J., et al., "Poly (amidoamine) hyperbranched systems: synthesis, structure and characterization," Polymer. 40, 1279–1297 (1999)]. Intrinsic viscosity measurements demonstrated that hyperbranched amidoamine polymer have much lower stiffness, which helps to explain the chain flexibility of hyperbranched polymers [Hawker, C. J., In Macromolecular Architectures, Vol. 147, pp 113–160 (1999)].

During HD synthesis, chloroethyl amine reacts with primary amines or secondary amines of PEI core, resulting in a random, tree-like branched structure. As demonstrated previously, the reactivity of a chain end of dendrimer is higher than the chain end reactivity of a hyperbranched polymer. To increase the rate of reaction between the functional end groups and chloroethyl amine, a large excess of chloroethyl amine in alkaline conditions was used. The excess of chloroethyl amine or its cyclic byproduct was easily removed using ultrafiltraion.

Figure 2:
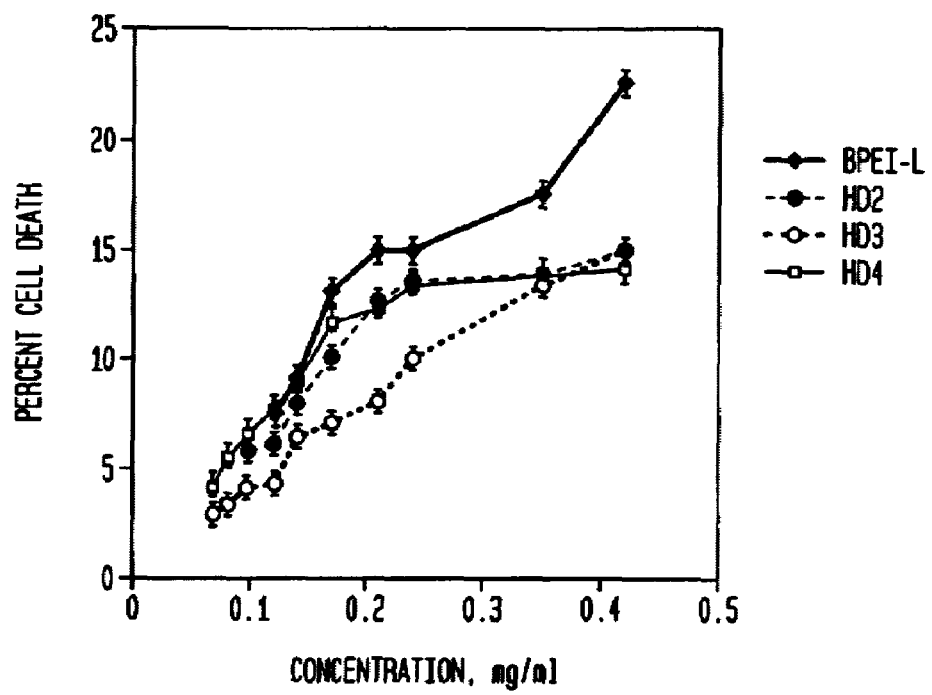
FIG. 2 shows the cytotoxicity in COS-1 cells as a function of concentrations measured using CytoTox96 non-radioactive assay (Promega) for the polymers of FIG. 1 and a control. Complexes were added to cells with growth media and incubated for 48 h without changing media. Results represent the average of four independent experiments.

Spectral NMR data was used to express the relative ratio of linear to branched structures, calculated from the integrals of secondary and tertiary amines. It is known that that highly branched, commercially available PEI with the high molar mass ranging from 25K to 800K have secondary to tertiary amine ratio of less than 1.2. The ratio measured in the case of hyperbranched dendron of the invention suggests that successive aminoethylation resulted in an increase of branching (Table 1). Thus, the increased branching enables the process to incorporate more secondary and tertiary amines than present in commercially available PEI core. Importantly, we observed a concomitant reduction of cytoxicity of hyperbranched dendrons compared to initial PEI core (FIG. 2). As reported previously, low molecular weight PEI (MW 10 KD) at a concentration of 0.1 mg/ml for 24 h causes cell death of 70% of cells, whereas high molecular PEI (MW ~25 KD) caused death of almost 100% of cells at the same concentration. In a separate study, a 25K branched PEI at a concentration of 0.1 mg/ml showed a ~90% cell death after 24 hr where a 52% hydrolyzed linear poly(2-ethyl 2-oxazoline) showed only a 20% cell death because of the high content of tertiary amines present in the backbone of the polymer. In the examples presented, at 0.1 mg/ml the hyperbranched polymers (HD2 to HD4 in the examples below) resulted in a 10% cell death. The higher cell viability in the presence of HD could be a result of the increase of secondary and tertiary amine content in the polymer which is comparable to hydrolyzed linear poly(2-ethyl 2-oxazoline).

TABLE 1

Properties of branched poly (ethylene imine) and hypebranched dendrons

| Polymer | MW[a] (kD) | PDI[b] | 1°:2°:3° amine[c] |
| --- | --- | --- | --- |
| BPEI-L | 9.5 | 2.46 | 2.68:1.58:1 |
| HD2 | 11.7 | 2.34 | 2.13:1.42:1 |
| HD3 | 13.7 | 2.32 | 1.96:1.31:1 |
| HD4 | 15 | 2.25 | 1.76:1.24:1 |

[a]MW = weight average molecular weight. Molecular weight was based on PEO standard, solvent 0.1 M ammonium acetate, flow rate 1 ml/min;
[b]PDI = polydispersity index;
[c]ratio of primary:secondary:tertiary amino groups calculated from $^{13}$C NMR spectra.

Figure 3:
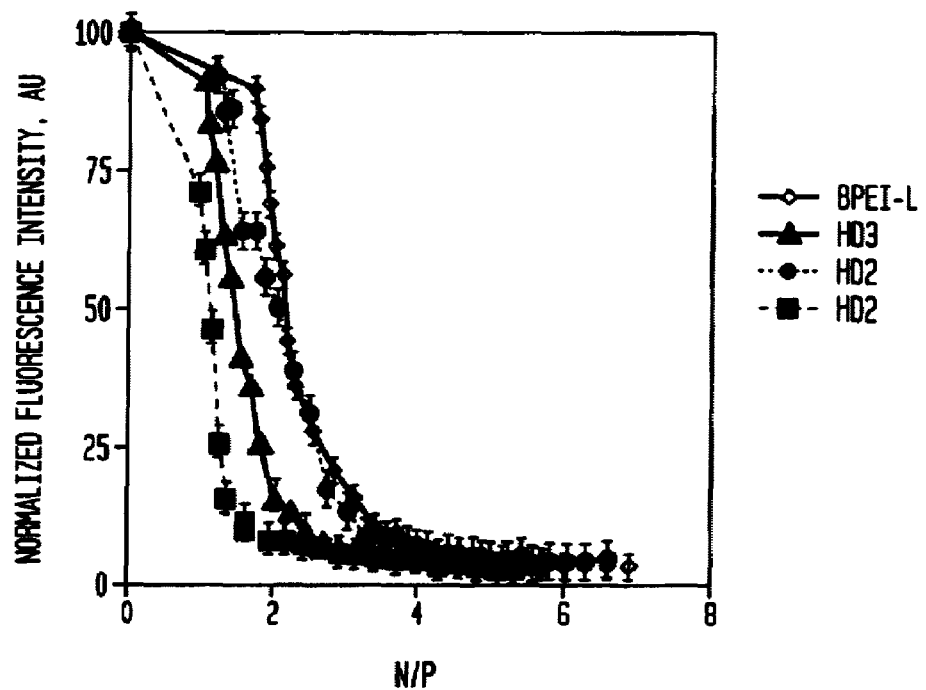
FIG. 3 shows a fluorescence profile of ethidium bromide displacement from hyperbranched polymer-DNA complexes of the invention and others. The legend denotes complexes formed between BPEI-L; HD4; and HD2. The y-axis represents the normalized fluorescence intensity. Results are averaged of three separate experiments.

In contrast to a classic PAMAM dendrimer, the random open structure of the polymers of the invention helps to maintain flexible architecture. Again, while not limiting the invention to one mode of operation, the inventors hypothesize that this flexible architecture enables efficient interaction of the polymer with DNA. Through the consecutive aminoethylation (from HD2 to HD4), the surface charge as well as the interior core of the polymers are changed. This result in differences in a DNA neutralization complex composition. We found that the increase of ethyleneimine content in HD resulted in similar titration behavior of HDs in ethidium bromide displacement experiments with the exception of the position of the neutralizing point (FIGS. 1 and 3). Therefore, at a specific concentration, different HDs have different surface charges because of the different branching order. This results in a dramatic change of N/P ratio corresponding to a half-maximal displacement of ethidium bromide. This observation is a consequence of more ethyleneimine moieties bound to BPEI backbone. For hyperbranched polymers HD3 and HD4, the obtained N/P ratios suggest the formation of a tight complex between the polymer and DNA. The overall increase in secondary and tertiary amine content in HD helps to maintain almost the same buffering capacity compared to BPEI-L (data not shown) but much higher buffering capacity when compared to linear polyethyleneimine (LPEI), suggesting that hyperbranched polymers could still retain endosomal disruption capability.

Hydrodynamic diameter measurements demonstrated small sizes of HD complexes (100 nm in diameter), supposedly due to the flexibility of hyperbranched dendron molecules. Interestingly, the data shows that in contrast to BPEI-L, particle size of HD complexes with DNA increased at a much slower rate or remained almost constant. Moreover, this effect was observed over a prolonged period of time (FIG. 5B). These results were relevant for further transfection experiments. It is possible that transfection efficiency depends on the combination of available charge as well as the size of the complex, which could explain why HD2-DNA complexes have the comparable size to HD4, but show lower transfection efficiency. The transfection data suggested that the HD-DNA complex could tolerate the presence of other negatively charged serum proteins that may compete for HD with DNA. This was not the case if a high molecular mass PEI was used in the presence of the serum. Hyperbranched polymers have a much higher branching order compared to BPEI-L. Concurrently, because of the uncontrolled branching HDs, are flexible which potentially increases transfection efficiency.

It has been reported previously that branched cationic polymers transfect cells because of the high buffering capacity of the amines present on these polymers, which leads to the release of DNA from the endosome. Such lysosomotropic agents have been observed to induce osmotic swelling and lysis in response to the endosomal local pH drop. Hyperbranched dendrons contain three different types of nitrogen, allowing the polymer to collapse, or to swell, depending on the magnitude of local pH change. Endosomal swelling due both to polymer expansion and osmotic induced swelling from protonation of amines causes endosomal rupture and the release of the complex or DNA into the cytoplasm (using lysosomotropic agents). This may explain why the hyperbranched polymer D4 has much higher transfection efficiency than the less branched core BPEI-L at much lower N/P ratios (FIG. 6). The optimized N/P ratio in the case of HD was 5–6 times lower than in the case of BPEI-L pointing to a much lower amount of the polymer needed for high transfection efficiencies.

Since the complex of HD with plasmid vectors show exceptional stability, we decided to test whether during storage the complex retains the ability to transfect cells (FIG. 8). The results suggest that that "aged" complex attains a more compact structure which could help in preserving its activity.

The question of whether stable complexes of plasmids with HD polymers will be efficient in gene transfer in vivo is also addressed. As a recent report suggested, in vivo bioluminescent imaging can be used to detect gene expression after non-viral gene delivery in vivo. In mice, seven consecutive days of luciferase imaging suggested that HD4 could induce a prolonged gene expression which reaches maximum at 72 hours in the liver and lymph nodes (FIG. 9B). Both HD4 and HD3 appear to be more efficient than either BPEI-L or "naked" DNA. Since both complexes bear only weak positive charge, we expected less interaction with blood components and lung endothelium. The latter could be the reason for low expression in the lung. Correlative luciferase activity measurements in tissue extracts (FIG. 9C) and histology also pointed to the expression of luciferase in the lymph node cells, the majority of positive cells located on the periphery and around germinal centers (FIG. 9D). The distribution of positive cells in the tissue argues for the ability of HD-based complexes to transfect organs located at the sites distant to the injection site, presumably, because of the small size and weak positive charge.

The data demonstrates that by attaching additional secondary and tertiary amino groups to a commercially available polyethyleneimine core it is feasible to "tune" the molecular structure of PEI to achieve a substantial increase of transfection ability with the concomitant lower cytotoxicity in vitro. The advantages that may be found in HD vectors over initial branched PEI can include: 1) the high transfection efficiency at low N/P ratios; 2) the formation of small stable complexes with DNA; 3) the tolerance of serum; 4) overall low toxicity of transfection conditions as the amounts of HD needed to achieve high transfection efficiency are low. Finally, the data in animals show that HD-based complexes have a potential for systemic and targeted transfection in vivo.

The materials and methods used, as well as a description of the results obtained, follows:

Materials and Methods

Materials and analytical methods. Polyethyleneimine (BPEI-L) (average molecular weight 10 kD; "L" stands for low molecular weight) was obtained from Polysciences, Inc. (Warrington, Pa.) and purified by ultrafiltration using 30K NMWC cartridge. Molecular mass of polymers was estimated using a PL aquagel-OH 40 8 μm column (Polymer Laboratories Inc, Amherst, Mass.) eluted with 100 mM ammonium acetate (pH 7) on a Varian ProStar HPLC coupled with refractive index (RI) detector at 30° C. Molecular mass was measured using polyethylene oxide standards. Weight average molecular mass was computed using a standard approach [Flory, P. J. *Principles of polymer chemistry*; Cornell University Press: Ithaca, N.Y., 1953]. Proton and $^{13}$C NMR were recorded using D$_2$O solutions by Spectral Data Service (Champaign, Ill.) at 400 MHz for $^1$H and 100 MHz for $^{13}$C spectra, respectively. D-luciferin was purchased from Xenogen (Alameda, Calif., USA).

Synthesis of PEI-Dendron

Hyperbranched Dendron 2 (HD2): Ten grams (0.086 mol) of 2-chloroethylamine hydrochloride (CEA, Acros, Pittsburgh, Pa.) were dissolved in 25 ml of water under stirring; 5 g (0.125 mol) of sodium hydroxide were added to this solution and the solution mixture was stirred at the room temperature and added drop-wise into the reaction flask equipped with a condenser and containing a 10% solution of 10 g BPEI-L. The reaction mixture was stirred for 1 h at 50° C. Sodium hydroxide solution (25%, 10 ml) was then added to the reaction mixture and temperature was raised to 90° C., refluxed for 5 h and stirred another 12 h at room temperature. The low molecular weight HD2 was purified by ultrafiltration using 30K NMWC cartridge (A/G Technology Co, Framingham Mass.) and freeze-dried.

Hyperbranched dendrons 3 and 4 (HD3 and HD4): HD2 (3.5 g) was reacted with 10 g of CEA in the presence of sodium hydroxide as described above. The purified product was used for HD4 synthesis. HD4 was prepared by repeating the procedure above using HD3 as a starting material.

Preparation of dendron-DNA complexes. The reporter plasmid, pCMV-Luc (3.2 MDa, 5.12 kb) encoding firefly luciferase was propagated in *E. coli*, DH5α and purified using Megaprep columns (Qiagen, Valencia, Calif.). Plasmid integrity was confirmed by gel electrophoresis in agarose. DNA concentration and purity was determined by measuring absorbance at 260 nm and 280 nm. The complex was prepared using 1 μg pCMV-Luc plasmid DNA with varying amounts of polymers in TE buffer at pH 7.1 for 1 h before loading onto a 0.7% agarose gel. Ethidium bromide titration studies were performed using F-4500 Fluorescence spectrophotometer Hitachi, Danbury, Conn.). The excitation and emission wavelengths for ethidium bromide dispalcement titration were 366 nm and 591 nm, respectively. Briefly, 10 μg DNA and 2 μg ethidium bromide solution (0.4 mg/ml) were mixed in 2 ml of TE buffer (pH 7.1). Polymer solution was added in 4–5 μl aliquots (1.06 mg polymer/ml). After adding polymer solution, the mixture was incubated at room temperature for 3 min for equilibriation and the fluorescence intensity was measured. Two consecutive measurements were performed and intensity values were averaged.

The size of the complexes was determined using Zetasizer 1000HSA (Malvern Instruments Inc, Southborough, Mass.) using a 633 nm laser source at a fixed angle of 90°. Complexes were prepared in 0.25M sucrose. All complexes were made by adding respective amount of dendron solution (~3 mg/ml 0.25M Sucrose solution) to DNA 20 μg/ml in TE buffer. The particle size was measured using 500 μl of complex solution at 25° C. Data was collected after two consecutive measurements. The change of particle size was measured for 3 weeks. All complexes were stored at 4° C.

Cell culture. COS-1 cells were propagated in Dulbecco's modified Eagle's medium with 4 mM L-glutamine, 1% penicillin-streptomycin and 10% fetal bovine serum.

Neuroprogenitor-derived cells, C17.2 (a generous gift of Dr. E. Snyder, Harvard Medical School) were propagated as described in [Snyder, E. Y., et al., "Multipotent Neural Cell-Lines Can Engraft and Participate in Development of Mouse Cerebellum," *Cell.* 68, 33–51 (1992)]. Human umbilical venous endothelial cells (HUVEC) were cultured using EGM2 (Cambrex Bio Science, Baltimore, Md.).

Transfection experiments. HD polymers were dissolved in 0.25M sucrose solutions (~3 mg/ml) and stored at 4° C. Polymer-DNA complexes were formed by adding polymer solutions to DNA solutions. Maximum volume for complex was adjusted to 50 μl by adding 0.25M sucrose solution. Weight ratios of hyperbranched dendron-to-nucleic acid was based on the calculation of total charge present in each component taking into the account molecular masses and degree of polymerization, i.e. the number of total nitrogen present in hyperbranched polymer vs. the number of phosphates present in the nucleic acid. For example, 1 µg of plasmid DNA solution (0.74 mg/ml) was assumed to have $0.19 \times 10^{16}$ negative charges. One µg of HD4 solution (3.3 mg/ml stock solution in 0.25 M sucrose) was assumed to have $1.35 \times 10^{16}$ positive charges. To obtain the theoretical charge ratio N/P=1, we mixed 0.15 µg of HD4 solution prepared by dilution polymer stock solution (3 mg/ml), with one µg of DNA (0.74 mg DNA/ml). We calculated N/P ratio assuming that total nitrogen (i.e. primary, secondary and tertiary amines) contained within a single HD molecule, as well as all phosphates of DNA are taking part in the complex formation.

Superfect cell transfection reagent (Qiagen, Valencia, Calif.) was used as a standard in our experiments. Superfect reagent and DNA complex with Superfect were diluted using a 0.25 M sucrose solution.

Cell transfection. Transfections with HD-plasmid DNA complexes were performed and the results were analyzed using standard assay for Iluciferase activity expression (Luciferase assay reagent, Promega, Madison, Wis.). Various amounts of hyperbranched polymer in 0.25M sucrose solution were added to the plasmid solution (0.5 µg pCMV-luc DNA in 30 µl of 0.1 TE buffer), mixed and incubated at room temperature for 30 min. Cells were plated at a density of 10,000 cells/well in 96 well plates, 24 h prior to transfection. Before the addition of complexes, medium was replaced by fresh 100 µl of serum containing media. The complexes were then added to each well. The total volume did not exceed 150 µl/well. The transfection was carried for either 4 h or 48 h at 37° C. In the case of 4 h transfection, the complete growth medium was replaced with the fresh serum-containing medium followed by another 48 h incubation. In the case of 48 h transfection, no medium change was performed. Luciferase activity in cell lysates was determined using Microlumat LB96P (EG&G Berthold) by adding 50 µl of luciferin substrate (Promega, Madison, Wis.) to 25 µl of cell lysate in each well using an automated injector (n=3 independent experiments for each transfection reagent). Luciferase activity was integrated over 10 s with 2 s intervals. The protein concentration was measured in the rest of 25 µl cell lysate using standard protein assay reagent Pierce-Endogen, Rockford, Ill.). Results were expressed in relative light units per mg of cell protein.

Transfection after storage. The complexes of hyperbranched polymer were prepared at the same ratio as in the case of conventional transfection. Complexes were incubated 20 min at room temperature and then stored at 4° C. for 3 weeks. After 3 weeks complexes were used for transfection, which was carried out in the same way as described above. As control, freshly made complexes were used.

Transfection of dried complex. The complexes of hyperbranched polymer were prepared at the same ratio as in the case of conventional transfection. Complexes were incubated 20 min at room temperature and then quenched in liquid nitrogen. The frigid complex was lyophilized to obtain powdered complex and stored at 40C. Just before transfection it was dissolved in deionized water and the transfection was carried out in the same way as described above for both in vitro (see FIG. 10) and in vivo (see FIG. 11) transfections. As control, freshly made complexes were used.

Cytotoxicity. Cells were plated at the same density as above. Cytotoxicity assays (n=4 experiments) were performed using standard CytoTox 96 Non-radioactive cytotoxicity assay (Promega, Madison, Wis.), i.e. a colorimetric method based on lactate dehydrogenase release (LDH).

Flow Cytometry. Various amounts of HD polymers in 0.25M sucrose solution were added to the plasmid solution (1.5 µg pCMV-GFP DNA in 30 ml of 0.1 TE buffer), mixed and incubated at room temperature for 30 min. Cells were plated at a density of 40,000 cells/well in 12 well plates, 24 h prior to transfection. Before the addition of complexes, medium was replaced by fresh 800 µl of serum-containing media. The 100 µl complexes were then added to each well. The total volume did not exceed 900 µl/well. After 6 h, the complete growth medium was replaced with the fresh serum-containing medium followed by another 48 h incubation. After 48 h of transfection, cells were subjected to fluorescence microscopy. Alternatively, cells were trypsinized and resuspended in 2% formalin-PBS solution for flow cytometry analysis (FACSCalibur, Beckton-Dickinson, Lexington Ky.).

In vivo CCD camera imaging of Luciferase reporter gene expression. Hyperbranched polymers (HD4 and HD3) were used for complex formation with 50 µg of plasmid DNA at N/P 6.3 and 9.1, respectively, in 200 µl of 5% glucose containing 20 mM Hepes (pH 5.5). A complex with BPEI-L was obtained at N/P 6.3. The complexes were injected intravenously via the tail vein of 4–6 week old female nude mice. Animals (n=3) were imaged for 7 days beginning at 1-day post IV injection. For imaging, animals were anesthetized i.p. using ketamine/xylazine. After anesthesia, the animals were injected i.p with 200 µl of 4.5 mg D-luciferin. After 5 min, the animals were placed in the imaging chamber coupled with cryogenically cooled CCD camera system (Rooper Scientific, Trenton, N.J.). A light image of the animal was obtained using polychromatic illumination. The luciferase activity within animal was then measured by recording the CCD photon counts for 15 min. Following data acquisition, post-processing was performed using image display and analysis suite developed in IDL (Research Systems Inc., Boulder, Colo.). Regions of interest were defined using an automatic intensity contour procedure to identify bioluminescence signals with intensities significantly greater than the background. For visualization purposes, bioluminescence images were fused with the corresponding white light images in a transparent pseudo-color overlay, permitting correlation of areas of bioluminescence with anatomy.

Ex vivo luciferase activity. After imaging for 3 days the HD4 complex injected animals were sacrificed and the organs were harvested for analysis performed as in Manthorpe, M., et al., "Gene therapy by intramuscular injection of plasmid DNA: studies on firefly luciferase gene expression in mice," *Hum Gene Ther.* 4, 419–431 (1993). The relative light unit obtained was normalized to organ weight. All data are reported as mean±SEM.

Histology. Submandibular lymph nodes were dissected for histology 3 days post injection. The tissue rinsed with PBS and frozen using Histo Prep (Fisher Scientific). Cryosections (thickness –6 µm) were cut and treated using anti-luciferase goat polyclonal antibody conjugated with horseradish peroxidase (Abcam, Cambridge Mass.) according to the manufacturer's protocol. The sections were counter-stained using hematoxylin and eosin prior to mounting.

Results

Synthesis and characterization. General scheme of hyperbranched PEI synthesis is shown in FIG. 1. The obtained HB polymers were characterized using $^1$H and $^{13}$C NMR spectra that showed characteristic 2.5–2.8 ppm peak due to the methylene group (—CH$_2$) of the backbone. Since different amine substitutions on proton NMR spectra could not be efficiently separated for quantitative analysis, we used $^{13}$C spectra for quantitation. In the case of $^{13}$C all the structural elements showed well-separated signals in the typical area between 37 and 55 ppm.

The different amine percentages were calculated using the formula described in Pierre, T. S., et al. "C-13-Nmr Analysis of Branched Polyethyleneimine," *Journal of Macromolecular Science-Chemistry. A*22, 877–887 (1985); and von Harpe, A., et al. "Characterization of commercially available and synthesized polyethylenimines for gene delivery," *J. Control. Release*. 69, 309–322 (2000). We determined that commercially available branched BPEI-L has higher content of primary amines and the ratio of secondary-to-tertiary amine is 1.35 measured by $^{13}$C NMR (Table 1). The molecular weight of the material is 9.5K with a polydispersity index (PDI) of 2.46, and degree of polymerization of 221. After the first round of reaction of HD polymer with 2-chloroethyl amine in presence of a base, the molecular weight of the product increased to 11.7K and PDI was 2.34 (HD2). The increase of molecular weight is due to the conjugation of approximately 51-ethyleneimine groups. In the case of Dendron 3 (HD3) (mol mass 13.7K, PDI 2.32), and hyperbranched dendron 4 (HD4) (mol mass 15K, PDI 2.25), the number of ethyleneimine groups increased to 98 and 128 respectively. The resultant materials were purified from the non-reacted CEA using ultrafiltration, which insures the complete separation from the low-molecular weight amine impurities. Physical properties of the material changed from a liquid-like (low molecular weight branched PEI, BPEI-L) to a semisolid polymer (HD4). It should be mentioned that since size exclusion chromatography (SEC) tends to underestimate the true molecular masses of branched polymers, the molecular masses measured in our studies (Table 1) were somewhat lower than the exact molecular mass [Flory, P. J. *Principles of polymer chemistry*; Cornell University Press: Ithaca, N.Y., 1953].

Cytotoxicity. FIG. 2 shows the cytotoxicity results obtained using branched PEI (BPEI-L) and synthesized hyperbranched polymer. All cytotoxicity measurements were performed after 48 h of transfection without medium changes. In all cases, the toxicity was low even after a 48 hour-incubation. In the case of hyperbranched polymers in the moderate range of polymer concentrations (0.05 to 0.5 mg/ml) a maximum of 15% cell death was observed which is lower than BPEI-L.

Figure 4:
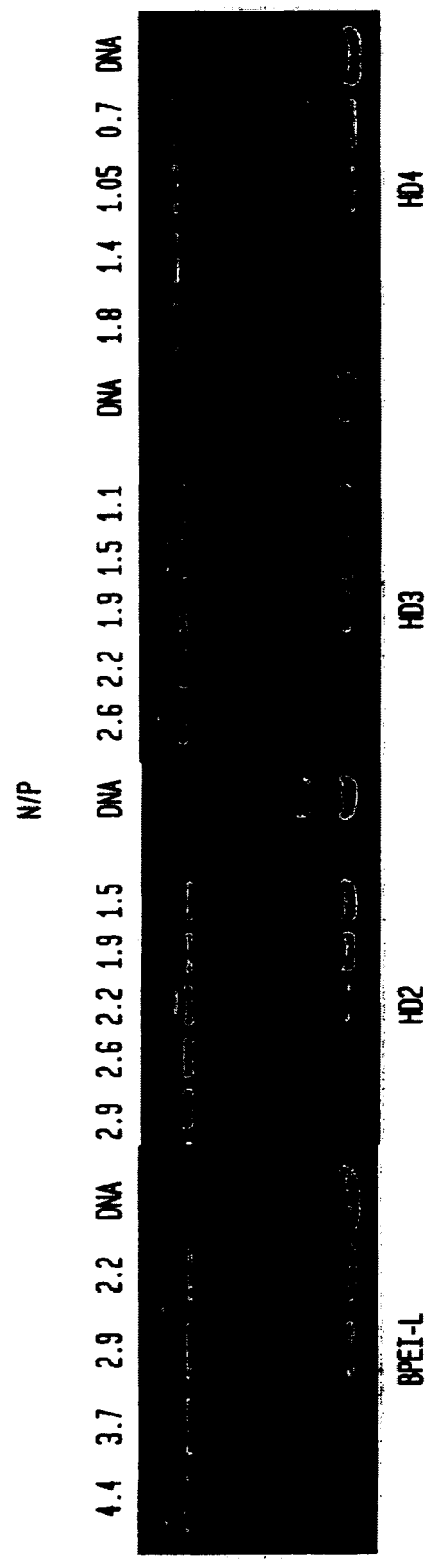
FIG. 4 illustrates agarose gel electrophoresis of pCMV-Luc plasmid complexed with BPEI-L (N/P 4.4, 3.7, 2.9, 2.2)

Complex formation. The formation of complexes was monitored by fluorescence microscopy using the ethidium bromide displacement method. At the N/P ratio of 2.30, the relative fluorescence decreased by approximately 50% for BPEI-L (FIG. 3). In case of hyperbranched dendron 2 (HD2), the same effect of fluorescence decrease was achieved at N/P of 2.27. In the case of hyperbranched dendron 3 (HD3) a 50% fluorescence intensity decrease was observed at the N/P of 1.70, and for hyperbranched dendron 4 (HD4) similar decrease was observed at N/P ratio of 1.23. To investigate the mobility of complexes, we studied the interaction between the positively charged polymers and the plasmid at the different charge ratio using electrophoresis. FIG. 4 shows the migration of DNA complexes with different hyperbranched polymers. The migration of DNA was partially retarded by branched BPEI-L at N/P 4.4, and at higher N/P ratios there was no detectable migration of the complex. In the case of hyperbranched dendron, the partial retardation of the migration was observed at N/P 2.9, 2.6 and 1.8, respectively, for HD2, HD3 and HD4 complexes. The migration of complexes, which were stored for 3 weeks at 4° C., was almost unchanged (data not shown).

In isotonic sucrose and glucose solutions the particle size of DNA-BPEI complexes at all N/P ratios ranged between 50 to 120 nm. A similar behavior was observed for all HD complexes (FIG. 5A). For HD4 complexes, particle size showed an increase from 90 nm to 160 nm when N/P ratio was decreased from 18 to 1. In the case of HD3 complex, the lowest particle size was observed at N/P ratio of 9.1, otherwise it varied slightly at different N/P. FIG. 5B shows the stability of the complexes measured for 3 weeks. In 150 mM NaCl solution complexes were not stable and usually coagulated within three hours. In the case of 5% glucose with 20 mM HEPES complexes were stable and usually smaller (approximately 40–60 nm) than isotonic sucrose solution (data not shown).

Transfection efficiency. To examine the potential of hyperbranched polymer for gene transfer to cells, we compared the transfection efficiency of BPEI-L and HDs with a standard commercially available dendrimer-based reagent (Superfect, Qiagen, Valencia, Calif.). Superfect is a very efficient transfection agent, especially in absence of serum in the cell culture medium. Since our main objective was to investigate the potential of hyperbranched polymers for the future in vivo gene delivery, we performed all transfections using 10% serum-containing media. The transfection efficiency was evaluated by luciferase reporter gene assay.

FIG. 6 compares the transfection of hyperbranched polymer and Superfect at 4 h after adding DNA complexes to cells in presence of serum. We used various N/P ratio for optimization of the transfection efficiency of hyperbranched polymer and Superfect. Hyperbranched dendron 4 (HD4) showed a very high transfection efficiency compared to other polymers in the presence of serum. When transfection efficiencies of the different HDs and branched polymers were compared, we found that HD4-mediated transfection was very high at N/P ~9 while BPEI showed maximum transfection efficiency at N/P ratio of ~33. Transfection efficiency of HD at 4 h in absence of serum was at least one order of magnitude higher than transfection in presence of serum (data not shown).

To obtain the further insight into the cytotoxicity effect and transfection efficiency, we carried out the transfection for 48 h without changing cell culture media. FIG. 7 shows the optimum N/P ratio based on 48 h transfection. Our data suggested that even after a prolonged co-incubation the transfection efficiency was still 5–6 fold higher than in the case of Superfect. All HDs as well as the branched PEI (BPEI-L) had higher transfection efficiencies in the presence of serum than with positive control transfection agent. The 48 h transfection data suggested that for HD4 at N/P=6.3 the highest transfection has been achieved, whereas for BPEI the best results were achieved at N/P=23.4 (FIG. 7). In the case of a 48 h transfection, we observed a 10-fold decrease of measured luminescence compared to the 4 h transfection. Polymers HD3 and HD4 gave comparable results with respect to transfection efficiency.

Transfection efficiencies of freshly prepared complexes and complexes stored for 3 weeks were then compared (FIG. 8). A comparison of transfection efficiencies at the optimized N/P ratios after a conventional 4 h transfection demonstrated that freshly prepared complexes have lower transfection efficiency than those stored for 3 weeks (FIG. 8A). At 48 h time point HD4 and HD3 showed the highest transfection efficiency at N/P=13 whereas the transfection efficiencies reached the highest levels at N/P ~23 and 19 for HD2 and BPEI-L, respectively (FIG. 8B). In all cases prolonged storage of complexes in sucrose solution resulted in ~8 fold higher transfection efficiencies.

Flow cytometry. To test the transfection efficacy of hyperbranched polymers for cells other than COS-1 we tested transfection efficiency in neuroprogenitor-derived C17.2 cell and human endothelial cell cultures. We used green fluorescent protein as a marker (Table 2). Both HD4 and HD3 were capable of transfecting 20–25% C17.2 and HUVEC cells compared to 40% cells in the case of COS-1.

TABLE 2

Percent of transfected cells by flow cytometry.

| Polymer* | COS1** | C17.2 | HUVEC |
|---|---|---|---|
| HD4 | ~40% | ~20–25% | ~20–25% |
| HD3 | ~30–40% | ~20–25% | ~20–25% |

*Cells were transfected for 6 h and incubated for 48 h as described in Materials and Methods.
**Histograms were analyzed using CellQuest software (ten thousand cells/analysis were used).

In vivo gene expression. To test the in vivo gene delivery efficacy we relied on long-term transfection results in selecting N/P ratios. As it is evident from FIG. 7, HD4 and HD3 showed the highest transfection efficiency at N/P 6.3 and 9.1 respectively. We selected these N/P ratios for a preliminary study and prepared a complex with 50 μg DNA. In the case of BPEI-L we noticed that the complex made at the optimized N/P=23 showed a profound toxicity after the injection. Since it is known that BPEI (molar mass 25K) showed less toxicity and better transfection in animals at N/P 6–8, we selected N/P ratio of 6.3. All complexes were stabilized in 20 mM HEPES/5% glucose solution.

FIG. 9A shows the marker gene expression profile in vivo using non-invasive luminescence imaging. We monitored the expression profile in the same group of animals repeatedly for seven days. As pseudo-color map demonstrates, in the case of HD4 complex gene expression was the highest. The main "hot spots" of luciferase expression were found in the liver and neck, and in the lymph node region. BPEI-L-based complex and "naked" DNA alone showed a much lower expression profile than hyperbranched dendron-based complexes. FIG. 9B shows the change of photon counts over a period of seven days. Both HD4 and HD3 showed highest photon counts at 3–5 days either around the liver or in the neck regions. FIG. 9C shows the luciferase assay of HD4 animal of liver and neck (submandibular) lymph node region which correlates with the gene expression profile obtained by luminescence imaging. Other organs did not show any measurable luciferase activity. Histology of lymph node tissue samples performed using frozen sections showed many immunoperoxidase-positive cells located on the periphery of lymph nodes. The positive cells were absent in lymph nodes of control animals or in animals injected with plasmid DNA only (FIG. 9D).

CONCLUSION

While not limiting the invention beyond what is recited in the claims below, the invention described herein includes polymers, complexes and processes that include hyperbranched dendron polymers. Hyperbranched polymers have densely branched tree-like structures and a large number of reactive groups. The tree-like structures of the hyperbranched polymers of the invention are emphasized by the nomenclature "dendron," derived from the Greek word for tree. These polymers typically consist of a core, from which branches extend three dimensionally in space, forming a more or less spherical or rod-shaped structure depending upon the type of core used. As distinct from dendrimers (which require absolute control of all synthesis steps), the hyperbranched dendron polymers of the invention are produced by an iterative process that is uncontrolled, meaning that the exact structure of the molecule will be random, while, as explained above, amine groups are located so as to provide the desired reactivity. The hyperbranched dendron molecules of the invention are distinguished in the description above over known hyperbranched dendron molecules in terms of their structure, their properties, and the results obtained when using the inventive molecules in the further experiments described.

In certain compositions of the present invention, a nucleic acid is included. The nucleic acid can be either a deoxyribonucleic acid or a ribonucleic acid. The sequences in question can be of natural or artificial origin, and in particular genomic DNA, cDNA, mRNA, tRNA, rRNA, siRNA, hybrid sequences or synthetic or semi-synthetic sequences. In addition, the nucleic acid can be very variable in size, ranging from oligonucleotide to chromosome. These nucleic acids may be of human, animal, vegetable, bacterial, viral, and the like, origin. They may be obtained by any technique known to a person skilled in the art, and in particular by the screening of libraries, by chemical synthesis or alternatively by mixed methods including the chemical or enzymatic modification of sequences obtained by the screening of libraries. They can, moreover, be incorporated into vectors, such as plasmid vectors.

For the purposes of the invention, therapeutic gene is understood, in particular, to mean any gene coding for a proteinaceous product having a therapeutic effect. The proteinaceous product thus encoded can be a protein, a peptide, and the like. This proteinaceous product can be homologous with respect to the target cell (that is to say a product which is normally expressed in the target cell when the latter is not suffering from any pathology). In this case, the expression of a protein makes it possible, for example, to remedy an insufficient expression in the cell or the expression of a protein which is inactive or feebly active on account of a modification, or alternatively to overexpress the said protein. The therapeutic gene may also code for a mutant of a cell protein, having enhanced stability, modified activity, and the like. The proteinaceous product may also be heterologous with respect to the target cell. In this case, an expressed protein may, for example, supplement or supply an activity which is deficient in the cell, enabling it to combat a pathology, or stimulate an immune response. The therapeutic gene may also code for a protein secreted into the body.

The therapeutic gene can also be an antisense gene or sequence, whose expression in the target cell enables the expression of genes or the transcription of cellular mRNAs to be controlled. Such sequences can, for example, be transcribed in the target cell into RNAs complementary to cellular mRNAs and can thus block their translation into protein. Antisense sequences also comprise sequences coding for ribozymes, which are capable of selectively destroying target RNAs.

The compositions and processes of the invention are also well suited to delivery of siRNA into cells in vitro and in vivo for therapeutic, diagnostic and/or investigatory purposes. RNA interference (RNAi) is a phenomenon in which a small double-stranded RNA (referred as small interference RNA or siRNA) can knock down the expression of its corresponding gene. RNAi has been observed in plant, *C. elegans* and *Drosophila* for a number of years and it been recently discovered that RNAi also works in mammalian systems. Small interference RNA (siRNA) is 19–22 nt double-stranded RNA that generally works by cleaving and destroying its cognate RNA. siRNA first assembles into RNA-induced silencing complexes (RISCs), and it then activates the complex by unwinding its RNA strands. The unwound RNA strands subsequently guide the complex to the complementary RNA molecules, where the complex cleaves and destroys the cognate RNA, which results in RNAi phenomenon. Applications of RNAi using the complexes and processes of the present invention include: a stable cell line with a specific gene knocked-out so that its phenotype can be studied; a knock-out mouse line can be established using transgenic siRNA method; siRNA can be put into a vector with an inducible promoter to study its effect; and siRNA can be delivered in vivo and used for gene therapy purposes.

Nucleic acid molecules used with the invention may also include, for example, sequences permitting the expression of the therapeutic gene and/or of the gene coding for the antigenic peptide in the desired cell or organ. These sequences can be the ones which are naturally responsible for expression of the gene in question when these sequences are capable of functioning in the infected cell. They can also be sequences of different origin (responsible for the expression of other proteins, or even synthetic sequences). For example, they can be promoter sequences originating from the genome of the cell which it is desired to infect. Similarly, they can be promoter sequences originating from the genome of a virus. In addition, these expression sequences may be modified by the addition of activation or regulatory sequences or sequences permitting a tissue-specific expression.

Moreover, the nucleic acid can also contain, especially upstream of the therapeutic gene, a signal sequence directing the therapeutic product synthesized into the pathways of secretion of the target cell. This signal sequence can be the natural signal sequence of the therapeutic product, but it can also be any other functional signal sequence, or an artificial signal sequence.

Advantageously, complexes of the invention described herein having a hyperbranched dendron polymer and a nucleic acid molecule can have a small size. In particular, polymers of the invention have been shown to condense with nucleic acid plasmids and molecules into nanostructures with a size of less than or equal to 100 nm, and in certain circumstances, as low as 50 nm, or in the range of 50 to 70 nm. This small size, among other advantages, can allow greater penetration of the complex in vivo to provide desired gene expression or other activity in desired locations within a mammal, such as, for example, in the lymph nodes—a result that heretofore has not been achieved using non-viral vectors.

Other advantages of certain complexes of the invention include their ability to provide lasting therapeutic effects in vivo, with gene expression shown over extended periods of time, and the ability of the complex to be lyophilized and stored dry. The dried complex can later be used with excellent results. In addition, the complexes of the invention have been shown to have uniquely lasting stability and, in particular, remain stable in the presence of serum.

The examples presented herein were generated using an in vivo mouse model system in which gene expression is reasonably correlated to gene expression in humans, and in mammals more generally.

Each of the references and documents (including any manufacturer's specifications, instructions, etc.) cited to or referenced herein, as well as any in the provisional application from which this application claims priority, is hereby expressly incorporated herein by reference. Such incorporated documents and their teachings can be used with the invention described herein and are expressly not admitted to be prior art.

The invention being thus disclosed and illustrative embodiments depicted herein, further variations and modifications of the invention will occur to those skilled in the art. In particular, it should be clear that all of the properties and characteristics of the hyperbranched polymers described above can be combined in any way, and that such properties and characteristics and similarly be applied to compositions or complexes that include the hyperbranched polymer, as well as to methods for synthesizing or using such polymers, compositions or complexes. All such variations and modifications are considered to be within the scope of the invention, as defined by the claims appended hereto and equivalents thereof.

What is claimed is:

1. A polymer comprising:
   a surface defined by the polymer;
   a branched polyethyleneimine (B-PEI) core within the surface;
   a plurality of primary amine groups at the surface; and
   a plurality of secondary and tertiary amine groups positioned at the core;
   wherein the polymer is a flexible hyperbranched dendron polymer.

2. The polymer of claim 1, wherein the polymer has a molecular weight of greater than or equal to about 10 kD.

3. The polymer of claim 2, wherein the polymer has a molecular weight of less than or equal to about 25 kD.

4. The polymer of claim 3, wherein the polymer has a secondary to tertiary amine ratio of less than or equal to about 1.5 to 1.

5. The polymer of claim 4, wherein the polymer has a secondary to tertiary amine ratio of less than or equal to about 1.3 to 1.

6. The polymer of claim 4, wherein the polymer has a secondary to tertiary amine ration of greater than about 1.0 to 1.

7. The polymer of claim 4, wherein the polymer has a secondary to tertiary amine ration of greater than or equal to about 1.2 to 1.

8. The polymer of claim 1, wherein the polymer is made by a process comprising iterative attachment of ethyleneimine moieties to a branched polyethyleneimine core.

9. The polymer of claim 8, wherein the process increases the amount of secondary and tertiary amines in the polymer while maintaining a plurality of primary amines on the surface of the polymer.

10. The polymer of claim 8, wherein the process comprising iterative attachment of ethyleneimine moieties to a branched polyethyleneimine core comprises:
   (a) reacting polyethyleneimine with chloroethyl amine;
   (b) reacting the modified polyethyleneimine of step (a) with chloroethyl amine; and
   (c) reacting the modified polyethyleneimine of step (b) with chloroethyl amine.

11. A hyperbranched dendron polymer having a randomly branched structure, a molecular weight of about 10 to 25 kD, and a ratio of secondary to tertiary amine groups of less than or equal to about 1.5 to 1.

12. The polymer of claim 11, wherein the ratio of secondary to tertiary amine groups is less than or equal to about 1.3 to 1.

13. The polymer of claim 12, wherein the ratio of secondary to tertiary amine groups is greater than or equal to about 1.2 to 1.

14. The polymer of claim 12, wherein the molecular weight is greater than or equal to about 12 kD.

15. The polymer of claim 12, wherein the molecular weight is less than or equal to about 15 kD.

16. The polymer of claim 11, wherein the polymer comprises:
    a surface defined by the polymer;
    a polyethyleneimine core within the surface;
    a plurality of primary amine groups at the surface; and
    a plurality of secondary and tertiary amine groups positioned at the core.

17. The polymer of claim 11, wherein the polymer is made by a process comprising iterative attachment of ethyleneimine moieties to a branched polyethyleneimine core.

18. The polymer of claim 17, wherein the process increases the amount of secondary and tertiary amines in the polymer while maintaining a plurality of primary amines on a surface of the polymer.

19. The polymer of claim 18, wherein the process comprising iterative attachment of ethyleneimine moieties to a branched polyethyleneimine core comprises:
    (a) reacting polyethyleneimine with chloroethyl amine;
    (b) reacting the modified polyethyleneimine of step (a) with chloroethyl amine; and
    (c) reacting the modified polyethyleneimine of step (b) with chloroethyl amine.

20. A hyperbranched dendron polymer made by a process comprising iterative attachment of ethyleneimine moieties to a branched polyethyleneimine core, wherein the process increases the amount of secondary and tertiary amines in the polymer while maintaining a plurality of primary amines on a surface of the polymer.

21. The polymer of claim 20, wherein the process comprising iterative attachment of ethyleneimine moieties to a branched polyethyleneimine core comprises:
    (a) reacting polyethyleneimine with chloroethyl amine;
    (b) reacting the modified polyethyleneimine of step (a) with chloroethyl amine; and
    (c) reacting the modified polyethyleneimine of step (b) with chloroethyl amine.

22. The polymer of claim 20, wherein the polymer has a molecular weight of greater than or equal to about 10 kD.

23. The polymer of claim 22, wherein the polymer has a molecular weight of less than or equal to about 25 kD.

24. The polymer of claim 23, wherein the polymer has a secondary to tertiary amine ratio of less than or equal to about 1.5 to 1.

25. The polymer of claim 24, wherein the polymer has a secondary to tertiary amine ratio of less than or equal to about 1.3 to 1.

26. The polymer of claim 24, wherein the polymer has a secondary to tertiary amine ration of greater than about 1.0 to 1.

27. The polymer of claim 24, wherein the polymer has a secondary to tertiary amine ration of greater than or equal to about 1.2 to 1.

28. The polymer of claim 1, wherein the polymer is polydisperse.

29. The polymer of claim 11, wherein the polymer is a flexible hyperbranched dendron polymer.

30. The polymer of claim 11, wherein the polymer is polydisperse.

31. The polymer of claim 20, wherein the polymer is a flexible hyperbranched dendron polymer.

32. The polymer of claim 20, wherein the polymer is polydisperse.

\* \* \* \* \*